US012709710B2

(12) United States Patent
Jao et al.

(10) Patent No.: US 12,709,710 B2
(45) Date of Patent: Aug. 18, 2026

(54) LIQUID CRYSTALLINE COMPOUNDS

(71) Applicant: MERCK PATENT GmbH, Darmstadt (DE)

(72) Inventors: Chen-Wei Jao, Taipei (TW); Marc Sauer, Darmstadt (DE); Thorsten Kodek, Darmstadt (DE); Minghui Yang, Pudong New Area (CN); Rocco Fortte, Darmstadt (DE); Sven Christian Laut, Darmstadt (DE)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 19/280,007

(22) Filed: Jul. 24, 2025

(65) Prior Publication Data

US 2026/0028531 A1 Jan. 29, 2026

(30) Foreign Application Priority Data

Jul. 25, 2024 (WO) ................ PCT/CN2024/107669

(51) Int. Cl.

| | |
|---|---|
| ***G02F 1/1333*** | (2006.01) |
| ***C07D 333/68*** | (2006.01) |
| ***C07D 409/04*** | (2006.01) |
| ***C07D 409/10*** | (2006.01) |
| ***C09K 19/34*** | (2006.01) |
| ***G02F 1/00*** | (2006.01) |

(52) U.S. Cl.

CPC ........ *C09K 19/3491* (2013.01); *C07D 333/68* (2013.01); *C07D 409/04* (2013.01); *C07D 409/10* (2013.01); *G02F 1/0018* (2013.01)

(58) Field of Classification Search

CPC .......................... C09K 19/3491; G02F 1/1333

See application file for complete search history.

(56) References Cited

U.S. PATENT DOCUMENTS

| | | | | |
|---|---|---|---|---|
| 6,403,172 B1 * | 6/2002 | Wingen | ............ | C09K 19/3491 252/299.61 |
| 2026/0028531 A1 * | 1/2026 | Jao | .................... | C09K 19/3491 |

FOREIGN PATENT DOCUMENTS

| | | | | |
|---|---|---|---|---|
| CN | 108018049 A | | 5/2018 | |
| CN | 120005633 A | * | 5/2025 | ........... G02F 1/1333 |
| CN | 120923446 A | | 11/2025 | |
| DE | 102004053279 A1 | | 6/2005 | |

OTHER PUBLICATIONS

Becker "Merck Liquid Crystals, Physical Properties of Liquid Crystals", Status Nov. 1997, 60 pages.

Extended European Search Report dated Dec. 8, 2025, issued by the European Patent Office in corresponding European Application No. 25190626.9-1014, (6 pages).

* cited by examiner

*Primary Examiner* — Geraldina Visconti

(74) *Attorney, Agent, or Firm* — Buchanan Ingersoll & Rooney PC

(57) ABSTRACT

Liquid-crystalline compounds with a terminal 5,6-difluoro-benzo[b]thiophene ring as provided by formula I, liquid crystal mixtures using the compounds, the use of the compounds in an electro-optical display, particularly in an active-matrix display based on the IPS or FFS effect, and liquid crystal displays that contain a liquid crystal material of this type.

12 Claims, No Drawings

LIQUID CRYSTALLINE COMPOUNDS

CROSS-REFERENCE TO RELATED APPLICATIONS

This is a U.S. nonprovisional patent application filed under 35 U.S.C. § 111(a), claiming priority benefit under 35 U.S.C. § 119(a) of and to PCT Application No. PCT/CN2024/107669, filed Jul. 25, 2024, the contents of which document are incorporated herein by reference in their entirety and for all purposes.

FIELD OF INVENTION

The invention relates to benzothiophene compounds of formula I

I

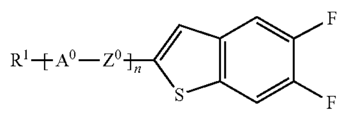

wherein the parameters have the meaning given in the text below, the use thereof in an electro-optical medium and electro-optical display, particularly in an active-matrix display based on the IPS or the FFS (fringe field switching) effect using dielectrically positive liquid crystals, and to displays of this type which contain a liquid-crystalline medium of this type.

IPS and FFS displays using dielectrically positive liquid crystals are well known in the field and have been widely adopted for various types of displays like e. g. desk top monitors and TV sets, but also for gaming, mobile, and automotive applications.

Industrial application of this effect in electro-optical display elements requires LC phases which have to meet a multiplicity of requirements. Particularly important here are chemical resistance to moisture, air and physical influences, such as heat, radiation in the infrared, visible and ultraviolet regions, and direct (DC) and alternating (AC) electric fields.

Furthermore, LC phases which can be used industrially are required to have a liquid-crystalline mesophase in a suitable temperature range and low viscosity.

None of the series of compounds having a liquid-crystalline mesophase that have been disclosed hitherto includes a single compound which meets all these requirements. Mixtures of two to 25, preferably three to 18, compounds are therefore generally prepared in order to obtain substances which can be used as LC phases.

Development in the area of liquid-crystalline materials is far from complete. In order to improve the properties of liquid-crystalline display elements, attempts are constantly being made to develop novel compounds which enable such displays to be optimised.

Liquid crystalline media having a positive dielectric anisotropy for IPS and FFS have been frequently described in patent publications. Compounds of these media often include fluorinated carbon atoms having a "$-CF_2-$" structure.

Benzo[b]thiophens as liquid crystal materials are disclosed in DE 10 2004 053 279 A1. These previously disclosed benzothiophenes and benzofurans are substituted by fluorine in a different pattern or by other substituents.

The phase range of the liquid-crystal mixture must be sufficiently broad for the intended application of the display. The response times of the liquid-crystal media in the displays should be as low as possible, especially for video, animated simulation and gaming applications. This is particularly important for displays for television or multimedia applications. In order to improve the response times, it has repeatedly been proposed in the past to optimise the rotational viscosity of the liquid-crystal media ($\gamma_1$), i.e. to achieve media having the lowest possible rotational viscosity.

However, the results achieved here are inadequate for many applications and therefore make it appear desirable to find further optimisation approaches.

SUMMARY OF INVENTION

An object of the present invention was to provide compounds having advantageous properties for use in liquid-crystalline media. Beside the physical properties required for the materials, their sustainability plays an increasing role, like environment-related properties (e.g. perfluoroalkyl content).

One object of the present invention was to find new stable compounds which are suitable as component of liquid crystalline media. In particular, the compounds should have a comparatively low viscosity and a high dielectric anisotropy at the same time. For many current mixing concepts in the field of liquid crystals, it is advantageous to use compounds with a positive dielectric anisotropy $\Delta\varepsilon$ in combination with a medium to high optical anisotropy.

With regard to the most diverse application areas of such compounds with high $\Delta\varepsilon$, it was desirable to have further compounds, preferably with high clearing point and low viscosity, which have precisely tailored properties to the respective applications.

The invention was therefore based on the object of finding new stable compounds which are suitable as components(s) of liquid crystalline media, in particular for e. g. TN, STN, IPS, FFS and TN TFT displays.

In addition, the compounds according to the invention should be thermally and photochemically stable under the conditions prevailing in the applications. As mesogens, they should enable a broad nematic phase in mixtures with liquid crystalline co-components and be excellently miscible with nematic base mixtures, especially at low temperatures. Substances with a low melting point and a low melting enthalpy are also preferred, since these properties in turn are indicative of the desirable properties mentioned above, such as high solubility, a wide liquid crystalline phase and a low tendency to spontaneous crystallization in mixtures at low temperatures. Solubility at low temperature, avoiding any crystallization, is particularly important for the safe operation and transport of displays in aircraft and in the open air.

Surprisingly, it has been found that it is possible to achieve environmental friendly liquid-crystal displays which have, in particular in IPS and FFS displays, a low threshold voltage with short response times, a sufficiently broad nematic phase, favourable birefringence ($\Delta n$) and, at the same time, a high transmission, high contrast, good stability to decomposition by heating and by UV exposure, and a stable, high VHR if use is made in these display elements of nematic liquid-crystal media, which comprise at least one compound of formula I.

The first embodiment of the current invention is a compound of formula I,

I

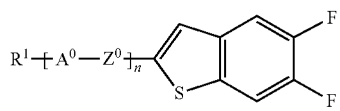

in which $R^1$ an alkyl radical having 1 to 15 C atoms, wherein one or more $CH_2$ groups, including terminal C atoms, in this radical may each be replaced, independently of one another, by —C≡C—, —CH═CH—,

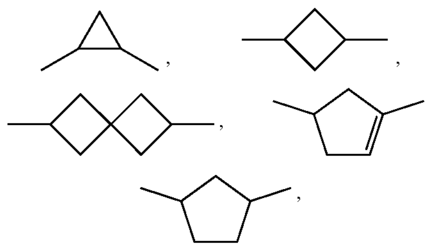

—O—, —S—, —(CO)—O— or —O—(CO)— in such a way that O or S atoms are not linked directly to one another, and in which, in addition, one or more H atoms may be replaced by F or Cl, $A^0$, independently of one another, on each appearance, denotes phenylene-1,4-diyl, in which, in addition, one or two CH groups may be replaced by N and one or more H atoms may be replaced by halogen, CN, $CH_3$, $CHF_2$, $CH_2F$, $OCH_3$, $OCHF_2$ or $OCF_3$, cyclohexane-1,4-diyl, in which, in addition, one or two non-adjacent $CH_2$ groups may be replaced, independently of one another, by O and/or S and one or more H atoms may be replaced by F, cyclo-hexene-1,4-diyl, bicyclo[1.1.1]pentane-1,3-diyl, bicyclo[2.2.2]octane-1,4-diyl, spiro[3.3]heptane-2,6-diyl, tetrahydropyran-2,5-diyl or 1,3-dioxane-2,5-diyl, $A^0$ preferably denotes

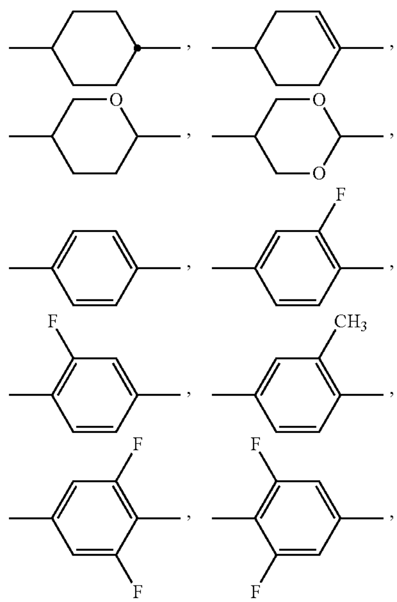

-continued

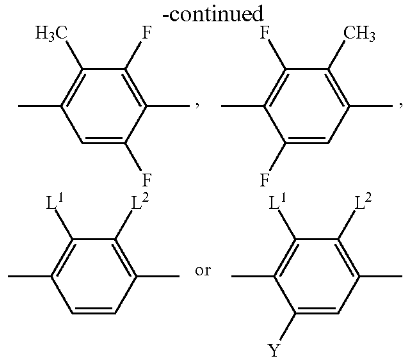

more preferably

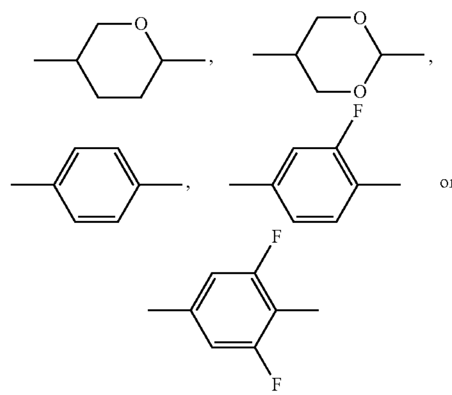

wherein $L^1$, $L^2$ each, independently of one another, denote F, Cl, $CH_3$ or $OCH_3$, preferably F,

Y $CH_3$, $CH_2CH_3$, $Z^0$ independently of one another, identically or differently, denotes a single bond, —$CH_2O$—, —(CO)O—, —$CF_2O$—, —$CH_2CH_2CF_2O$—, —$CF_2CF_2$—, —$CH_2CF_2$—, —$CH_2CH_2$—, —$(CH_2)_4$—, —CH═CH—, —CH═CF—, —CF═CF— or —C≡C—, and n denotes 1, 2 or 3, preferably 1 or 2.

A further embodiment of this invention is use of the compounds of formula I in liquid crystalline mixtures, particularly in positive dielectric mixtures (preferably IPS, FFS).

The compounds of formula I are distinguished by a surprisingly large positive dielectric anisotropy (Δs) and are therefore suitable, in particular, for use in TN-TFT displays, and in IPS- and FFS displays. The compounds have a comparatively low melting point, a very high clearing point and they exhibit very good compatibility with the conventional substances used in liquid-crystal mixtures for displays and are well soluble in such media. The compounds do not have any perfluoroalkyl groups in their structures, making them innocuous towards the environmental aspect of accumulation of perfluoroalkyl structured substances.

The compounds according to the invention preferably have a Δε of >9, preferably of >15 and particularly preferably a Δε of >17. The liquid-crystalline compounds in accordance with the present application preferably support a nematic phase and are used for nematic mixtures.

The invention also relates to liquid-crystalline media comprising one or more of the compounds of the formula I according to the invention. The liquid-crystalline media comprise at least two components. They are preferably obtained by mixing the components with one another. With the compounds according to the invention mixtures can be composed which are devoid of polyfluoro- or perfluoralkyl containing components.

The liquid-crystalline media according to the invention preferably comprise 2 to 40, particularly preferably 4 to 30, components as further constituents besides one or more compounds according to the invention. In particular, these media comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclo-hexylcyclohexanecarboxylic acid, cyclohexylphenyl esters of benzoic acid, of cyclo-hexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexanes, 1,4-biscyclohexylbenzenes, 4,4'-biscyclohexyl-biphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)ethanes, 1-cyclohexyl-2-biphenylethanes, 1-phenyl-2-cyclohexyl-phenylethanes, optionally halogenated stilbenes, benzyl phenyl ethers, tolans and substituted cinnamic acids. The 1,4-phenylene groups in these compounds may also be fluorinated.

The most important compounds suitable as further constituents of the media according to the invention can be characterised by the formulae 1, 2, 3, 4 and 5:

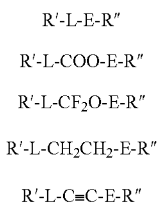

R′-L-E-R″ 1

R′-L-COO-E-R″ 2

R′-L-$CF_2$O-E-R″ 3

R′-L-$CH_2CH_2$-E-R″ 4

R′-L-C≡C-E-R″ 5

In the formulae 1, 2, 3, 4 and 5, L and E, which may be identical or different, each, independently of one another, denote a divalent radical from the group formed by the structural elements -Phe-, -Cyc-, -Phe-Phe-, -Phe-Cyc-, -Cyc-Cyc-, -Pyr-, -Dio-, -Py-, -G-Phe-, -G-Cyc- and their mirror images, where Phe denotes unsubstituted or fluorine-substituted 1,4-phenylene, Cyc denotes trans-1,4-cyclohexylene, Pyr denotes pyrimidine-2,5-diyl or pyridine-2,5-diyl, Dio denotes 1,3-dioxane-2,5-diyl, Py denotes tetrahydropyran-2,5-diyl and G denotes 2-(trans-1,4-cyclohexyl)ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe, Py and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

R' and/or R" each, independently of one another, denote alkyl, alkenyl, alkoxy, alkoxyalkyl, alkenyloxy or alkanoyloxy having up to 8 C atoms, —F, —Cl, —CN, —NCS or $—(O)_iCH_{3-k}F_k$, where i is 0 or 1 and k is 1, 2 or 3.

In a smaller sub-group of the compounds of the formulae 1, 2, 3, 4 and 5, R' and R" each, independently of one another, denote alkyl, alkenyl, alkoxy, alkoxyalkyl, alkenyloxy or alkanoyloxy having up to 8 C atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is referred to as group B, R" denotes —F, —Cl, —NCS or $—(O)_iCH_{3-k}F_k$, where i is 0 or 1 and k is 1, 2 or 3. The compounds in which R" has this meaning are referred to by the sub-formulae 1 b, 2b, 3b, 4b and 5b. Particular preference is given to those compounds of the sub-formulae 1 b, 2b, 3b, 4b and 5b in which R" has the meaning —F, —Cl, —NCS, —CF3, $—OCHF_2$ or $—OCF_3$.

In the compounds of the sub-formulae 1b, 2b, 3b, 4b and 5b, R' has the meanings indicated in the case of the compounds of the sub-formulae 1a to 5a and is preferably alkyl, alkenyl, alkoxy or alkoxyalkyl.

In a further smaller sub-group of the compounds of the formulae 1, 2, 3, 4 and 5, R" denotes —CN. This sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' has the meanings indicated in the case of the compounds of the sub-formulae 1a to 5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides compounds of the formula I according to the invention, the media according to the invention preferably comprise one or more compounds selected from groups A, B and/or C. The proportions by weight of the compounds from these groups in the media according to the invention are preferably:

- group A: 0 to 90%, preferably 20 to 90%, particularly preferably 30 to 90%;
- group B: 0 to 80%, preferably 10 to 80%, particularly preferably 10 to 65%;
- group C: 0 to 80%, preferably 0 to 80%, particularly preferably 0 to 50%;

where the sum of the proportions by weight of the compounds from groups A, B and C present in the media according to the invention is preferably 5 to 90% and in particular 10 to 90%.

The liquid-crystal mixtures according to the invention are prepared in a manner which is conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multibottle" systems.

Throughout this application and especially for the definition of $R^1$ etc. alkyl means an alkyl group, which may be straight-chain or branched. Each of these radicals is preferably straight-chain and preferably has 1, 2, 3, 4, 5, 6, 7 or 8 C atoms and is accordingly preferably methyl, ethyl, n-propyl, n-butyl, n-pentyl, n-hexyl or n-heptyl.

Throughout this application alkenyl means an alkenyl group, which may be straight-chain or branched and preferably is straight chain and preferably has 2, 3, 4, 5, 6 or 7 or 8 C atoms. Preferably it is vinyl, 1-E-alkenyl or 3-E- alkenyl, most preferably it is vinyl, 1-E-propenyl, 1-E-butenyl, 1-E-pentenyl, 3-butenyl or 3-E-pentenyl.

The compounds of the general formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for the said reactions. Use can be made here of variants which are known per se, but are not mentioned here in greater detail.

The compounds of formula I may in particular be synthesized as in the synthesis examples or in accordance with the following reaction schemes:

Scheme 1. General synthesis scheme for the preparation of benzothiophene compounds of the formula I wherein $A^0$ is benzene (optionally substituted by $L^{1-3}$).

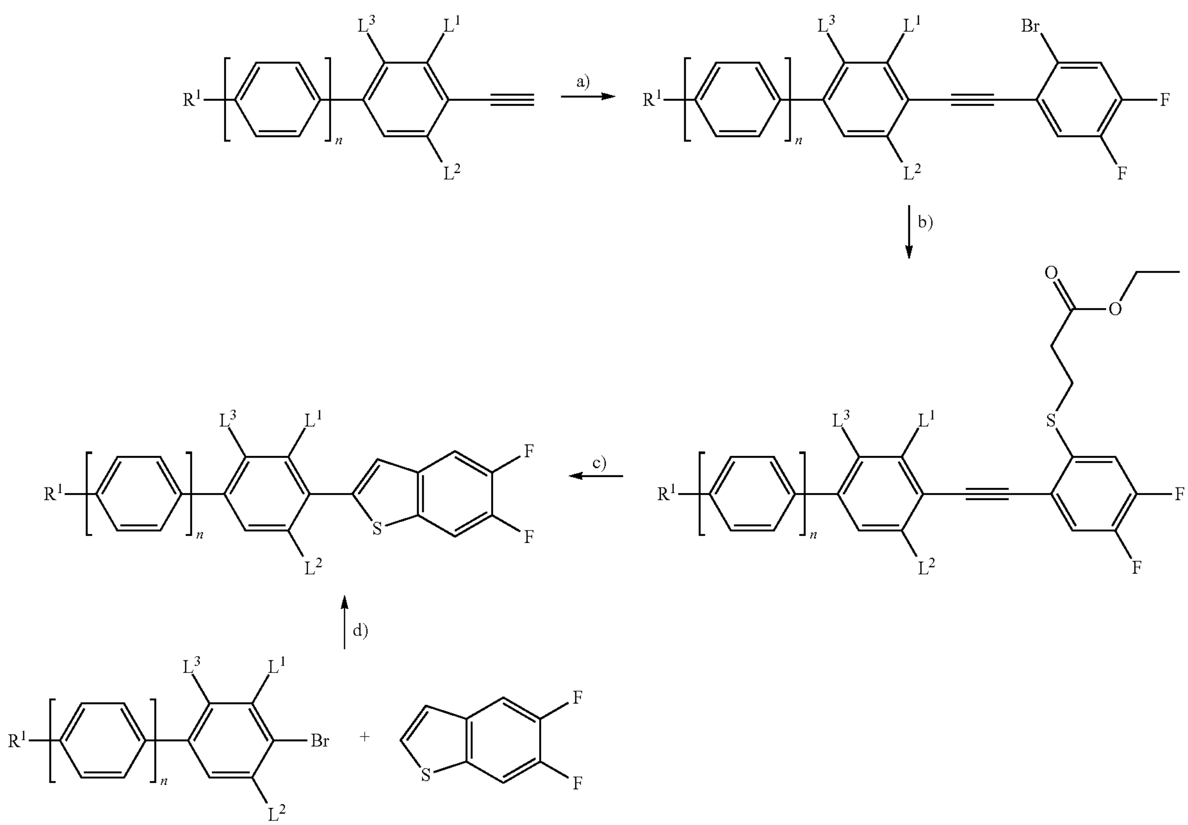

The variable groups are defined in accordance with formula I and $L^{1-3}$ are independently H, F or $CH_3$. Reaction details, a): Sonogashira reaction, b): Pd cross-coupling, c): cyclisation by strong base (KOtBu), d): heteroarylic Heck reaction.

Scheme 2. General synthesis scheme for the preparation of benzothiophene compounds of the formula I with saturated ring $A^0$.

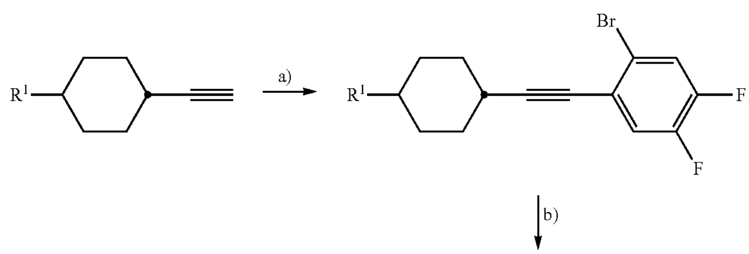

-continued

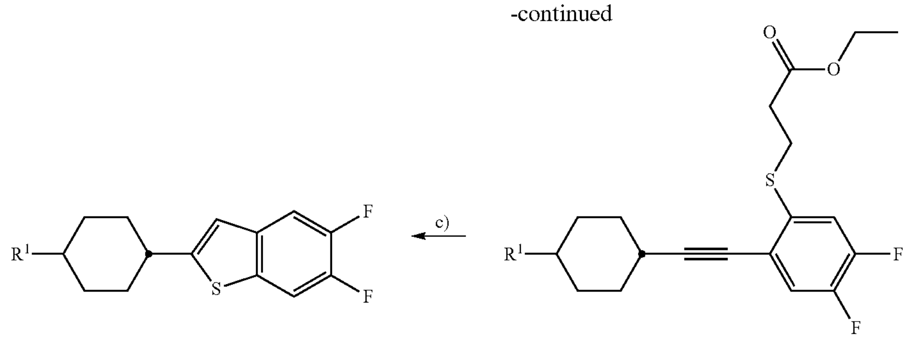

The variable groups are defined in accordance with formula I. Reaction details, a): Sonogashira reaction, b): Pd cross- coupling, c): cyclisation by strong base (KOtBu).

The invention therefore also relates to a process for the preparation of compounds of the formula I

I

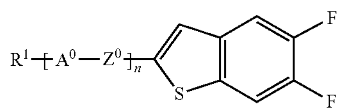

in which the groups are as defined above, which includes a process step in which a compound of the formula I-S

I-S

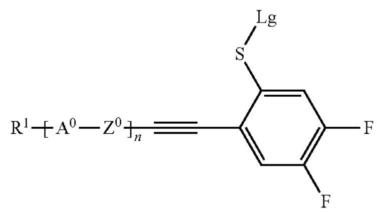

in which $R^1$, $A^0$, $Z^0$ and n are defined as for formula I, and

Lg is a leaving group, preferably a group defined as $R^1$ for formula I or a (poly)cyclic alkyl, more preferably an alkyl radical having 1 to 15 C atoms, wherein one or more $CH_2$ groups may each be replaced, independently of one another by —O—, —(CO)—O— or —O—(CO)— in such a way that O and S atoms are not linked directly to one another, most preferably $—(CH_2)_2(CO)OCH_2CH_3$ or $CH_3$, is reacted with a base to give a compound of the formula I.

Preferred bases are tert-butoxides of potassium, lithium or sodium and hydroxides of sodium, potassium or lithium.

The reaction can alternatively or in addition be induced by acids (trifluoroacetic acid), radical initiators, oxygen and/or silver oxide ($Ag_2O$).

The reaction methods and reagents used are in principle known from the literature. Further reaction conditions are revealed by the working examples. Further preferred process variants, not mentioned above, are revealed by the examples or the claims. The process and the subsequent work-up of the reaction mixture can basically be carried out as a batch reaction or in a continuous reaction procedure. The continuous reaction procedure encompasses, for example, reaction in a continuous stirred-tank reactor, a stirred-tank reactor cascade, a loop or cross-flow reactor, a flow tube or in a microreactor. The reaction mixtures are optionally worked up, as necessary, by filtration through solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

The invention furthermore relates to the use of compounds of formula I in a liquid-crystal display, in particular an IPS or FFS display.

Particular preference is given to liquid-crystal mixtures and liquid-crystalline media which have a nematic phase, in particular at room temperature (20° C.).

In a preferred embodiment of the present invention, the compound of formula I is selected from formula I-A and, alternatively, more preferably from the group of the compounds of the formulae I-a and I-b:

I-A

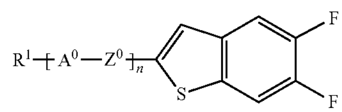

alternatively

I-a

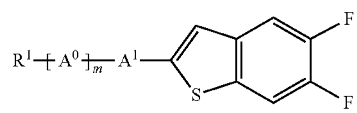

I-b

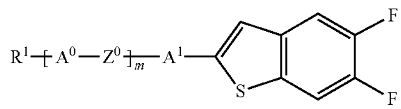

wherein the variables are defined as in formula I above and below, and m is 0, 1 or 2.

Particular preference is given here to compounds of formula I or I-A in which n is 1 or 2, preferably 2, and to compounds of formula Ia/Ib wherein m is 0 or 1, preferably 1. The group $A^1$ here preferably denotes phenylene (i.e. 1,4-phenylene), which is optionally fluorinated, particularly preferably a group of formula

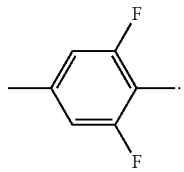

The group $A^0$ here preferably denotes a ring element selected from

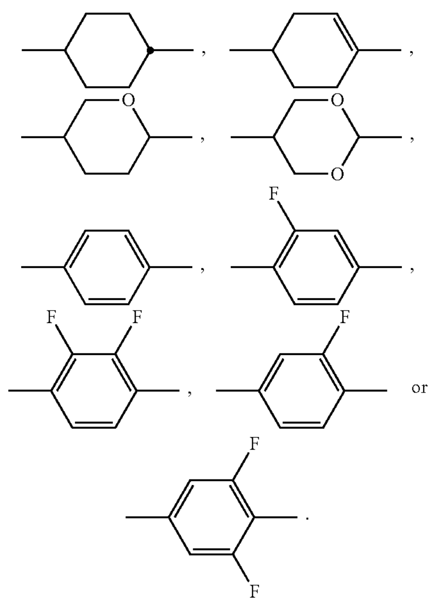

In the formulae I and in the related more specific formulae above and below compounds are preferred, wherein independently:

n is 1 or 2, $R^1$ is an alkyl radical having 1 to 7 C atoms, wherein one or more $CH_2$ groups, including terminal C atoms, in this radical may each be replaced, independently of one another, by —C≡C—, —CH═CH—,

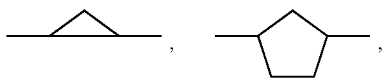

or —O— in such a way that O atoms are not linked directly to one another, and in which, in addition, one or more H atoms may be replaced by F, more preferably an alkyl radical having 2 to 7 C atoms.

In a preferred embodiment of the present invention the compounds of formula I are selected from the group of the compounds of the following formulae:

I-1

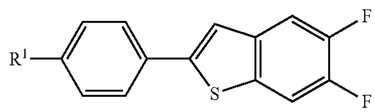

-continued

I-2

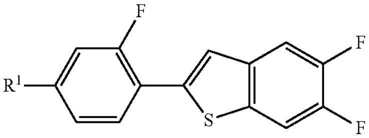

I-3

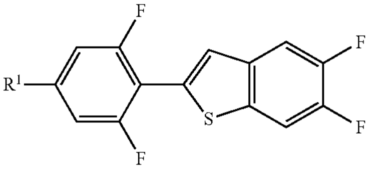

I-4

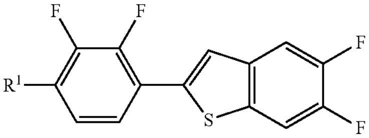

I-5

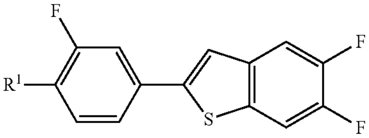

I-6

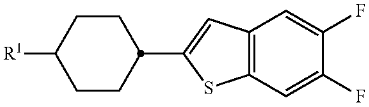

I-7

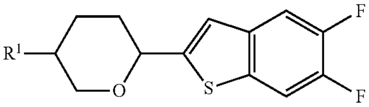

I-8

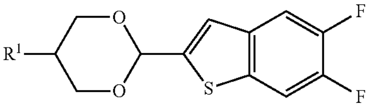

I-9

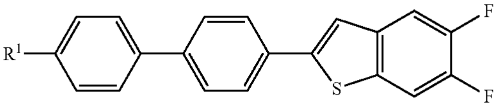

I-10

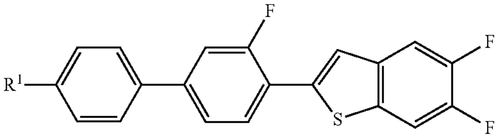

I-11

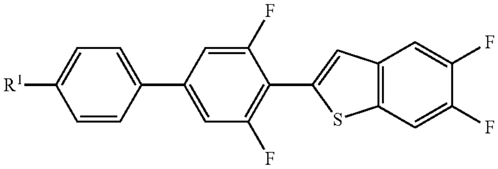

I-12

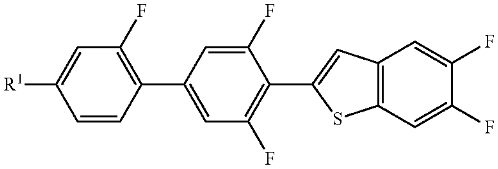

-continued

I-13

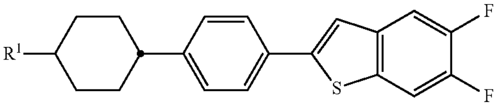

I-14

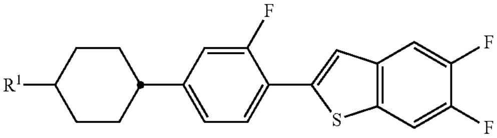

I-15

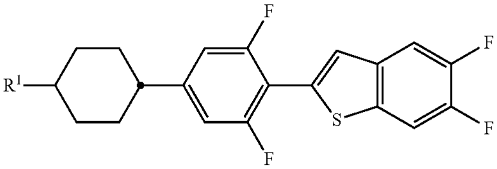

I-16

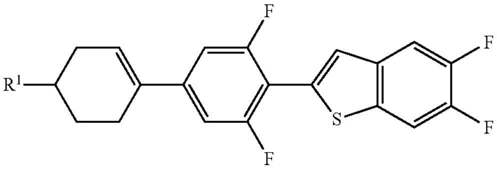

I-17

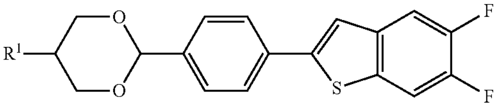

I-18

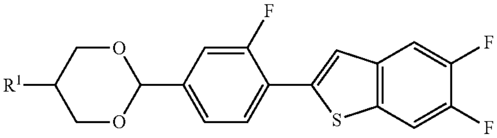

I-19

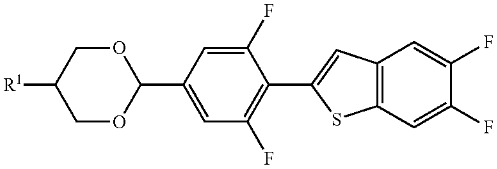

I-20

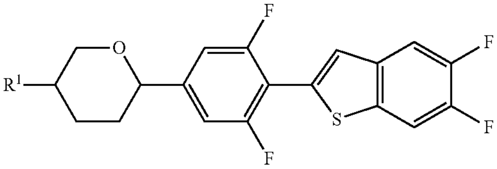

I-21

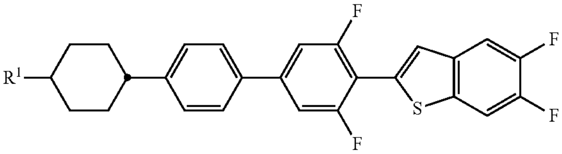

-continued

I-22

I-23

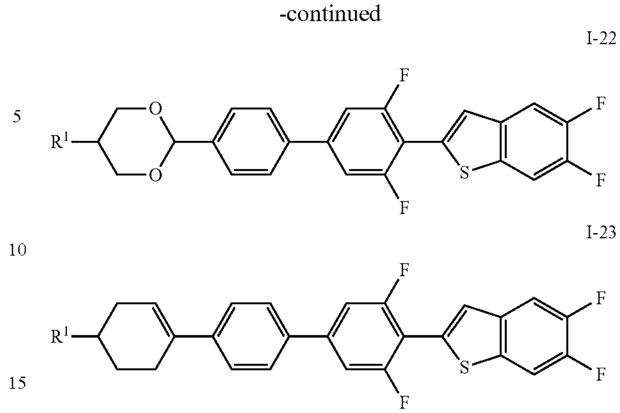

wherein $R^1$ is defined as for formula I above and below, including preferred definitions.

The invention furthermore relates to an electro-optical display having active-matrix addressing based on the IPS, FFS or UB-FFS effect, characterised in that it contains, as dielectric, a liquid-crystalline medium comprising at least on compound of formula I according to the invention.

DETAILED DESCRIPTION OF THE INVENTION

In the present application, the term "compounds", also written as "compound(s)", means both one and also a plurality of compounds, unless explicitly indicated otherwise.

For the present invention, the following definitions apply in connection with the specification of the constituents of the compositions, unless indicated otherwise in individual cases:

"comprise": the concentration of the constituents in question in the composition is preferably 5% or more, particularly preferably 10% or more, very particularly preferably 20% or more, "predominantly consist of": the concentration of the constituents in question in the composition is preferably 50% or more, particularly preferably 55% or more and very particularly preferably 60% or more, "essentially consist of": the concentration of the constituents in question in the composition is preferably 80% or more, particularly preferably 90% or more and very particularly preferably 95% or more, and "virtually completely consist of": the concentration of the constituents in question in the composition is preferably 98% or more, particularly preferably 99% or more and very particularly preferably 100.0%.

This applies both to the media as compositions with their constituents, which can be groups of compounds as well as individual compounds, and also to the groups of compounds with their respective constituents, the compounds. Only in relation to the concentration of an individual compound relative to the medium as a whole does the term comprise mean: the concentration of the compound or compounds in question is preferably 1% or more, particularly preferably 2% or more, very particularly preferably 4% or more.

For the present invention, "≤" means less than or equal to, preferably less than, and "≥" means greater than or equal to, preferably greater than.

For the present invention

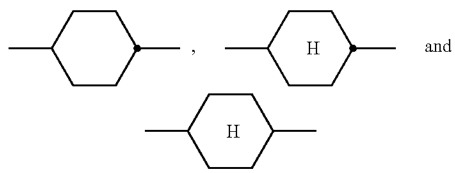

denote trans-1,4-cyclohexylene,

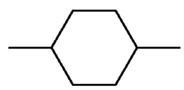

denotes a mixture of both cis- and trans-1,4-cyclohexylene and

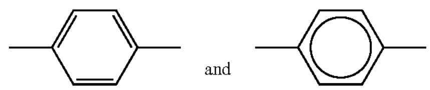

denote 1,4-phenylene.

In the present disclosure, the 2,5-disubstituted dioxane ring of the formula

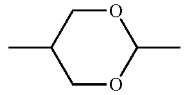

preferably denotes a 2,5-trans-configured dioxane ring, i.e. the substituents R are preferably both in the equatorial position in the preferred chair conformation. The 2,5-disubstituted tetrahydropyran of the formula

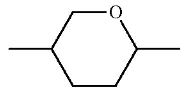

likewise preferably denotes a 2,5-trans-configured tetrahydropyran ring, i.e. the substituents are preferably both in the equatorial position in the preferred chair conformation.

For the present invention, the expression "dielectrically positive compounds" means compounds having a $\Delta\varepsilon$ of >1.5, the expression "dielectrically neutral compounds" means compounds having $-1.5 \leq \Delta\varepsilon \leq 1.5$ and the expression "dielectrically negative compounds" means compounds having $\Delta\varepsilon < -1.5$. The dielectric anisotropy of the compounds is determined here by dissolving 10% by weight of the compounds in a liquid-crystalline host and determining the capacitance of the resultant mixture in each case in at least one test cell having a cell thickness of 20 μm with homeotropic and with homogeneous surface alignment at 1 kHz. The measurement voltage is typically 0.5 V to 1.0 V, but is always lower than the capacitive threshold of the respective liquid-crystal mixture investigated.

The host mixture used for dielectrically positive and dielectrically neutral compounds is ZLI-4792 and that used for dielectrically negative compounds is ZLI-2857, both from Merck KGaA, Germany. The values for the respective compounds to be investigated are obtained from the change in the dielectric constant of the host mixture after addition of the compound to be investigated and extrapolation to 100% of the compound employed. The compound to be investigated is dissolved in the host mixture in an amount of 10% by weight. If the solubility of the substance is too low for this purpose, the concentration is halved in steps until the investigation can be carried out at the desired temperature.

All temperature values indicated in the present application, such as, for example, the melting point T(C,N), the smectic (S) to nematic (N) phase transition T(S,N) and the clearing point T(N,I), are indicated in degrees Celsius (° C.) and all temperature differences are correspondingly indicated in differential degrees (° or degrees), unless explicitly indicated otherwise.

All physical properties are and have been determined in accordance with "Merck Liquid Crystals, Physical Properties of Liquid Crystals", status November 1997, Merck KGaA, Germany, and apply for a temperature of 20° C., and $\Delta n$ is determined at 436 nm, 589 nm and at 633 nm, and $\Delta\varepsilon$ at 1 kHz, unless explicitly indicated otherwise in each case.

The rotational viscosity is determined using the rotating permanent magnet method and the flow viscosity in a modified Ubbelohde viscometer. For liquid-crystal mixtures ZLI-2293, ZLI-4792 and MLC-6608, all products from Merck KGaA, Darmstadt, Germany, the rotational viscosity values determined at 20° C. are 161 mPa·s, 133 mPa·s and 186 mPa·s respectively, and the flow viscosity values (ν) are 21 $mm^2 \cdot s^{-1}$, 14 $mm^2 \cdot s^{-1}$ and 27 $mm^2 \cdot s^{-1}$, respectively.

The dispersion of the materials may for practical purposes be conveniently characterized in the following way, which is used throughout this application unless explicitly stated otherwise. The values of the birefringence are determined at a temperature of 20° C. at several fixed wavelengths using a modified Abbe refractometer with homeotropically aligning surfaces on the sides of the prisms in contact with the material. The birefringence values are determined at the specific wavelength values of 436 nm (respective selected spectral line of a low pressure mercury lamp), 589 nm (sodium "D" line) and 633 nm (wavelength of a HE-Ne laser (used in combination with an attenuator/diffusor in order to prevent damage to the eyes of the observers. In the following table $\Delta n$ is given at 589 nm and $\Delta(\Delta n)$ is given as $\Delta(\Delta n) = \Delta n(436\ nm) - \Delta n(633\ nm)$.

The following symbols are used, unless explicitly indicated otherwise:

$n_e$ extraordinary refractive index measured at 20° C. and 589 nm, $n_O$ ordinary refractive index measured at 20° C. and 589 nm, $\Delta n$ optical anisotropy measured at 20° C. and 589 nm, $\lambda$ wavelength $\lambda$ [nm], $\varepsilon_\perp$ dielectric susceptibility perpendicular to the director at 20° C. and 1 kHz, $\varepsilon_\parallel$ dielectric susceptibility parallel to the director at 20° C. and 1 kHz, $\Delta\varepsilon$ dielectric anisotropy at 20° C. and 1 kHz, T(N,I) or clp. clearing point [° C.], ν flow viscosity measured at 20° C. [$mm^2 \cdot s^{-1}$], $\gamma_1$ rotational viscosity measured at 20° C. [mPa·s], $K_{11}$ elastic constant, "splay" deformation at 20° C. [pN], $K_{22}$ elastic constant, "twist" deformation at 20° C. [pN] ($K_{22}$% $K_{11}$), $K_{33}$ elastic constant, "bend" deformation at 20° C. [pN], $K_{av.}$ average elastic constant at 20° C. [pN] defined here as $$K_{av.} \equiv (3/2K_{11} + K_{33})/3 \approx (K_{11} + K_{22} + K_{33})/3,$$

LTS low-temperature stability of the phase, determined in test cells,

VHR voltage holding ratio.

The following examples explain the present invention without intending to limit it.

SYNTHESIS EXAMPLES

Synthesis Example 1

1

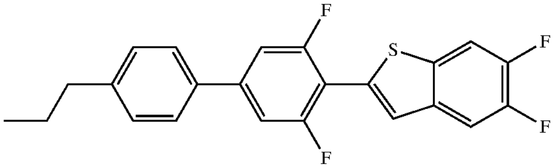

Compound 1 is prepared as follows.

a) Synthesis of Alkyne A

A

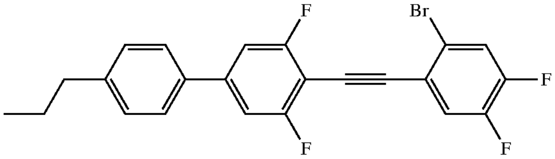

13.5 g (48.7 mmol) 1,2-dibromo-4,5-difluorobenzene is dissolved in 43.9 mL triethylamine. 1.11 g (1.59 mmol) $Pd_2Cl_2(PPh_3)_2$ and 302.2 mg (1.59 mmol) CuI is added, and the mixture is degassed with Argon and heated to 60° C. A solution of 8.30 g (31.73 mmol) literature known 4-ethynyl-3,5-difluoro-4'-propyl-1,1'-biphenyl dissolved in 50 mL degassed THF is added within 60 min and the reaction mixture is stirred under reflux overnight. After cooling to room temperature methyl-tert-butylether (MtBE) is added and the rection mixture is washed three times with saturated $NH_4Cl$-solution and the organic phases are combined and dried over $Na_2SO_4$, filtrated, and evaporated under vacuum. The remaining solid is purified via column chromatography (Heptane/MtBE 98:2) and the product is obtained as a white, crystalline solid.

MS TOF-MS EI+=446.027 b) Synthesis of Alkyne B

B

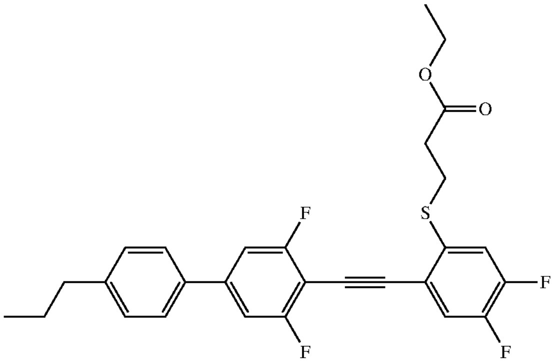

6.40 g (14.3 mmol) of alkyne A and 2.32 mL (18.0 mmol) ethyl-3-mercapto-propionate are dissolved in degassed 40 mL toluene. 5.10 g (37.0 mmol) $K_2CO_3$, 786.3 mg (1.43 mmol), oxydi-2,1-phenylenebisdiphenylphosphine and 675.4 mg (0.72 mmol) tris(dibenzylideneacetone)dipalladium are added and the reaction mixture is stirred under reflux for 4 h. After cooling to room temperature 20 g of silica gel (60 mesh) is added and the mixture is directly filtered over 400 g silica gel (60 mesh) and the product is obtained as a solid material.

MS EI=500.2 c) Synthesis of Benzothiophene 1

4.20 g (8.39 mmol) of alkyne B is dissolved in 40 mL THF and cooled to minus 78° C. and a solution of 847.40 mg (7.55 mmol) potassium tert-butoxide in 10 mL THF is added within 30 min which results in an orange-colored solution. After further 5 min the reaction mixture was poured in a mixture of water (500 mL), MtBE (500 mL) and 1 M HCl (10 mL). The organic phase is washed twice with water, with brine, dried over $Na_2SO_4$, filtered, and evaporated under vacuum. The slightly yellow raw product is purified by column chromatography with toluene and the product is obtained as a crystalline solid material.

MS EI=400.08

$^1$H NMR (500 MHz, DMSO) δ $^1$H NMR (500 MHz, $CDCl_3$) δ 7.75 (s, 1H), 7.64 (ddd, J=21.0, 10.1, 7.2 Hz, 2H), 7.57-7.51 (m, 2H), 7.36-7.24 (m, 5H), 2.68 (dd, J=8.5, 6.8 Hz, 2H), 1.77-1.65 (m, 2H), 1.01 (t, J=7.3 Hz, 3H).

Compound (1) has the following phase characteristics:

K 147 SmA 212 N 230 I $\Delta\varepsilon$: 22

$\Delta n$: 0.335

Synthesis Example 2

2

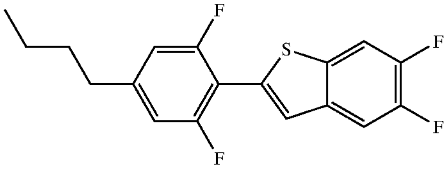

Compound 2 is prepared as follows.

5.00 g (29.35 mmol) 5,6-difluoro-1-benzothiophene and 10.0 g (35.3 mmol) 2-bromo-5-butyl-1,3-difluorobenzene are dissolved in 60.0 mL N,N-dimethylacetamide. 150 mg (0.66 mmol) palladium(II)diacetate and 6.00 g (43.41 mmol) $K_2CO_3$ is added and the reaction mixture is heated for 20 h at 130° C. (mixture turns dark at 100° C.). The reaction mixture is cooled to room temperature and diluted with a mixture of heptane and toluene (1:1). The organic layer is washed with brine and dried over $Na_2SO_4$, filtered and 25 g of ISOLUTE® sorbent is added and the solvent is removed under vacuum and the raw material is purified by successive column chromatography. The product is obtained as a crystalline solid.

MS APCl=338.075

$^1$H NMR (500 MHz, $CDCl_3$) δ 7.67-7.55 (m, 3H), 6.92-6.85 (m, 2H), 2.69-2.63 (m, 2H), 1.70-1.60 (m, 2H), 1.41 (h, J=7.3 Hz, 2H), 0.98 (t, J=7.3 Hz, 3H).

Compound 2 has the following phase characteristics:

K 85 I

Δε: 19

Δn: 0.196

γ: 74 mPa·s

Synthesis Example 3

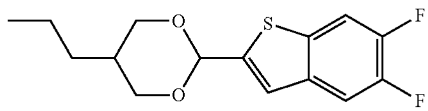

3

Compound 3 is prepared as follows.

2.50 g (21.15 mmol) 2-propylpropane-1,3-diol, 4.10 g (20.68 mmol) 5,6-difluoro-1-benzothiophene-2-carbaldehyde, is dissolved in 70 mL toluene and 120.0 mg (0.63 mmol) toluene-sulfonic acid monohydrate is added and the reaction is refluxed for 1 h. After cooling to room temperature toluene is added and the layers are separated. The organic layer is washed with brine, dried over $Na_2SO_4$ and filtered. The raw product is purified by column chromatography. The crystalline product is then crystallized out of heptane and isopropanol (melting point 149° C.).

$^1$H NMR (500 MHz, DMSO) δ 8.14 (dd, J=10.7, 7.4 Hz, 1H), 7.91 (dd, J=11.2, 7.8 Hz, 1H), 7.42 (s, 1H), 5.80 (s, 1H), 4.18-4.11 (m, 2H), 3.61-3.52 (m, 2H), 2.06-1.93 (m, 1H), 1.35-1.24 (m, 2H), 1.09-1.01 (m, 2H), 0.88 (t, J=7.3 Hz, 3H).

Compound 3 has the following phase characteristics:

K 149 I

Δε: 18

Δn: 0.297

Synthesis Example 4

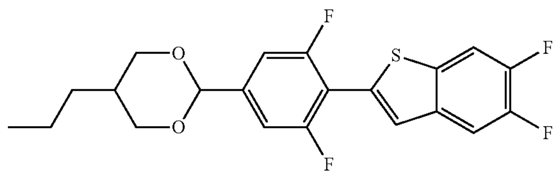

4

Compound 4 is synthesized according to the synthesis pathway for Synthesis Example 1.

$^1$H NMR (400 MHz, $CDCl_3$) δ 7.66 (s, 1H), 7.58 (ddd, J=17.7, 10.1, 7.2 Hz, 2H), 7.21-7.01 (m, 2H), 5.39 (s, 1H), 4.34-4.15 (m, 2H), 3.62-3.43 (m, 2H), 2.28-1.94 (m, 1H), 1.42-1.25 (m, 2H), 1.14-1.01 (m, 2H), 0.93 (t, J=7.3 Hz, 3H).

Compound 4 has the following phase characteristics:

K 163 N 196 I

Δε: 18

Δn: 0.1607

Further Compound Examples

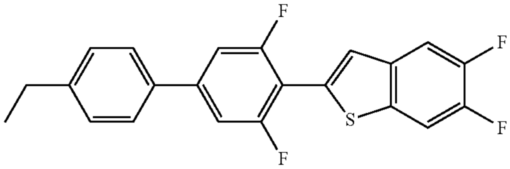

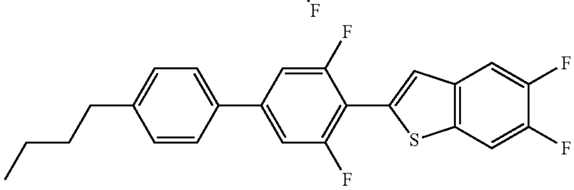

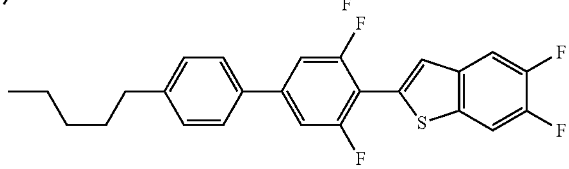

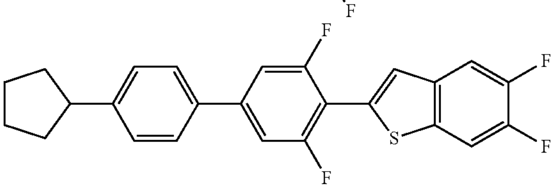

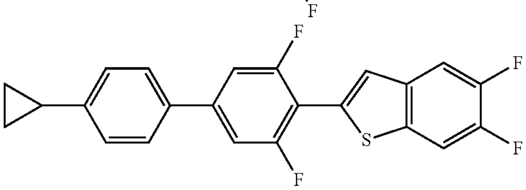

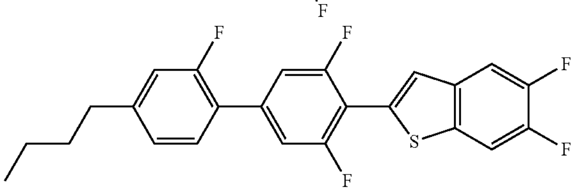

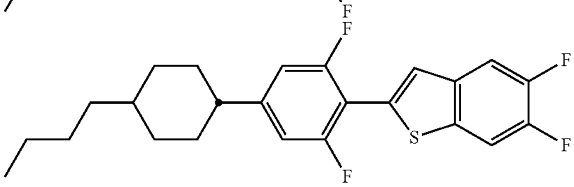

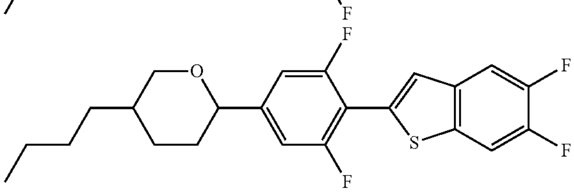

-continued

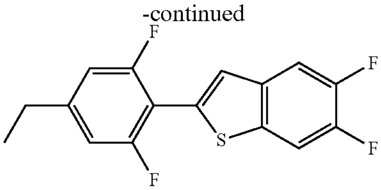

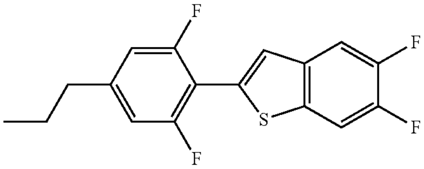

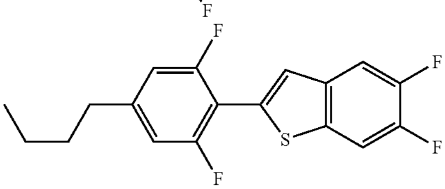

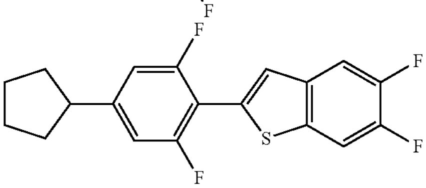

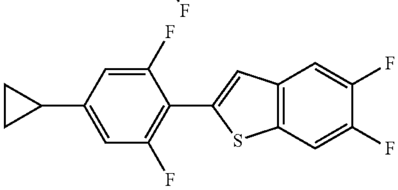

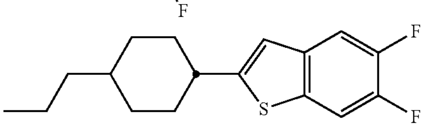

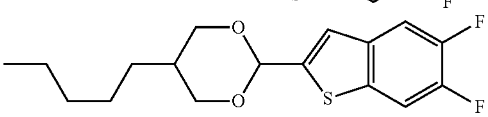

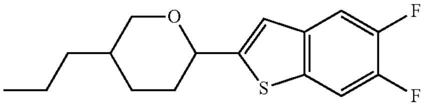

In the following table the following abbreviations for the end groups are used

| | |
|---|---|
| c-$C_3H_5$ | 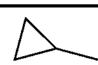 |
| c-$C_3H_5CH_2$ | 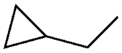 |
| c-$C_4H_7$ | 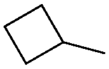 |
| c-$C_5H_7$ | 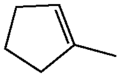 |
| c-$C_5H_9$ | 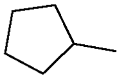 |

Further Exemplary Compounds

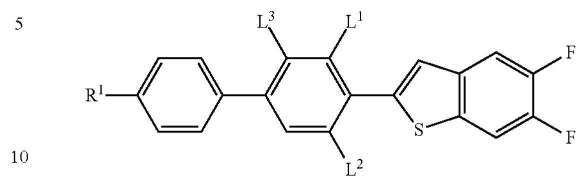

wherein the variables are as in the following table.

| No. | $R^1$ | $L^1$ | $L^2$ | $L^3$ |
|---|---|---|---|---|
| 1. | $CH_3$ | H | H | H |
| 2. | $C_2H_5$ | H | H | H |
| 3. | $n$-$C_3H_7$ | H | H | H |
| 4. | $n$-$C_4H_9$ | H | H | H |
| 5. | $n$-$C_5H_{11}$ | H | H | H |
| 6. | $n$-$C_6H_{13}$ | H | H | H |
| 7. | $n$-$C_7H_{15}$ | H | H | H |
| 8. | $n$-$C_8H_{17}$ | H | H | H |
| 9. | $c$-$C_3H_5$ | H | H | H |
| 10. | $c$-$C_3H_5$—$CH_2$ | H | H | H |
| 11. | $c$-$C_4H_7$ | H | H | H |
| 12. | $c$-$C_5H_7$ | H | H | H |
| 13. | $c$-$C_5H_9$ | H | H | H |
| 14. | $c$-$C_5H_9CH_2$ | H | H | H |
| 15. | $CH_2$═CH | H | H | H |
| 16. | $CH_3CH$═CH | H | H | H |
| 17. | $CH_2$═$CH(CH_2)_2$ | H | H | H |
| 18. | $CH_3CH$═$CH(CH_2)_2$ | H | H | H |
| 19. | $CH_3$ | F | H | H |
| 20. | $C_2H_5$ | F | H | H |
| 21. | $n$-$C_3H_7$ | F | H | H |
| 22. | $n$-$C_4H_9$ | F | H | H |
| 23. | $n$-$C_5H_{11}$ | F | H | H |
| 24. | $n$-$C_6H_{13}$ | F | H | H |
| 25. | $n$-$C_7H_{15}$ | F | H | H |
| 26. | $n$-$C_8H_{17}$ | F | H | H |
| 27. | $c$-$C_3H_5$ | F | H | H |
| 28. | $c$-$C_3H_5$—$CH_2$ | F | H | H |
| 29. | $c$-$C_4H_7$ | F | H | H |
| 30. | $c$-$C_5H_7$ | F | H | H |
| 31. | $c$-$C_5H_9$ | F | H | H |
| 32. | $c$-$C_5H_9CH_2$ | F | H | H |
| 33. | $CH_2$═CH | F | H | H |
| 34. | $CH_3CH$═CH | F | H | H |
| 35. | $CH_2$═$CH(CH_2)_2$ | F | H | H |
| 36. | $CH_3CH$═$CH(CH_2)_2$ | F | H | H |
| 37. | $CH_3$ | F | F | H |
| 38. | $C_2H_5$ | F | F | H |
| 39. | $n$-$C_3H_7$ | F | F | H |
| 40. | $n$-$C_4H_9$ | F | F | H |
| 41. | $n$-$C_5H_{11}$ | F | F | H |
| 42. | $n$-$C_6H_{13}$ | F | F | H |
| 43. | $n$-$C_7H_{15}$ | F | F | H |
| 44. | $n$-$C_8H_{17}$ | F | F | H |
| 45. | $c$-$C_3H_5$ | F | F | H |
| 46. | $c$-$C_3H_5$—$CH_2$ | F | F | H |
| 47. | $c$-$C_4H_7$ | F | F | H |
| 48. | $c$-$C_5H_7$ | F | F | H |
| 49. | $c$-$C_5H_9$ | F | F | H |
| 50. | $c$-$C_5H_9CH_2$ | F | F | H |
| 51. | $CH_2$═CH | F | F | H |
| 52. | $CH_3CH$═CH | F | F | H |
| 53. | $CH_2$═$CH(CH_2)_2$ | F | F | H |
| 54. | $CH_3CH$═$CH(CH_2)_2$ | F | F | H |
| 55. | $CH_3$ | F | H | F |
| 56. | $C_2H_5$ | F | H | F |
| 57. | $n$-$C_3H_7$ | F | H | F |
| 58. | $n$-$C_4H_9$ | F | H | F |
| 59. | $n$-$C_5H_{11}$ | F | H | F |
| 60. | $n$-$C_6H_{13}$ | F | H | F |
| 61. | $n$-$C_7H_{15}$ | F | H | F |
| 62. | $n$-$C_8H_{17}$ | F | H | F |

-continued

| No. | $R^1$ | $L^1$ | $L^2$ | $L^3$ |
|---|---|---|---|---|
| 63. | $c\text{-}C_3H_5$ | F | H | F |
| 64. | $c\text{-}C_3H_5—CH_2$ | F | H | F |
| 65. | $c\text{-}C_4H_7$ | F | H | F |
| 66. | $c\text{-}C_5H_7$ | F | H | F |
| 67. | $c\text{-}C_5H_9$ | F | H | F |
| 68. | $c\text{-}C_5H_9CH_2$ | F | H | F |
| 69. | $CH_2{=}CH$ | F | H | F |
| 70. | $CH_3CH{=}CH$ | F | H | F |
| 71. | $CH_2{=}CH(CH_2)_2$ | F | H | F |
| 72. | $CH_3CH{=}CH(CH_2)_2$ | F | H | F |

The invention claimed is:

1. A compound of formula I

I

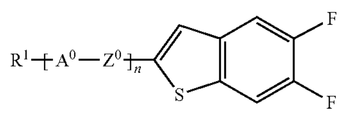

in which $R^1$ is an alkyl radical having 1 to 15 C atoms, wherein one or more $CH_2$ groups in this radical may each be replaced, independently of one another, by —C≡C—, —CH=CH—,

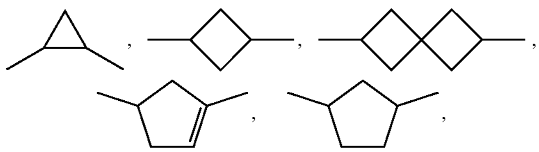

—O—, —S—, —(CO)—O—, —O—(CO)— in such a way that O or S atoms are not linked directly to one another, and in which, in addition, one or more H atoms may be replaced by F or Cl, $A^0$ independently of one another, on each appearance, denotes phenylene-1,4-diyl, in which, in addition, one or two CH groups may be replaced by N and one or more H atoms may be replaced by halogen, CN, $CH_3$, $CHF_2$, $CH_2F$, $OCH_3$, $OCHF_2$ or $OCF_3$, cyclohexane-1,4-diyl, in which, in addition, one or two non-adjacent $CH_2$ groups may be replaced, independently of one another, by O and/or S and one or more H atoms may be replaced by F, cyclohexene-1,4-diyl, bicyclo[1.1.1]pentane-1,3-diyl, bicyclo-[2.2.2]octane-1,4-diyl, spiro[3.3]heptane-2,6-diyl, tetrahydropyran-2,5-diyl or 1,3-dioxane-2,5-diyl, $Z^0$ independently denotes a single bond, $—CH_2O—$, —(CO)O—, $—CF_2O—$, $—CH_2CH_2CF_2O—$, $—CF_2CF_2—$, $—CH_2CF_2—$, $—CH_2CH_2—$, $—(CH_2)_4—$, —CH=CH—, —CH=CF—, —CF=CF— or —C≡C—, wherein $—CH_2O—$, —(CO)O—, $—CF_2O—$, $—CH_2CH_2CF_2O—$, —CH=CF—, and $—CH_2CF_2—$ may be inserted in any orientation, and n denotes 1, 2 or 3.

2. The compound according to claim 1, wherein $A^0$ is $A^0$

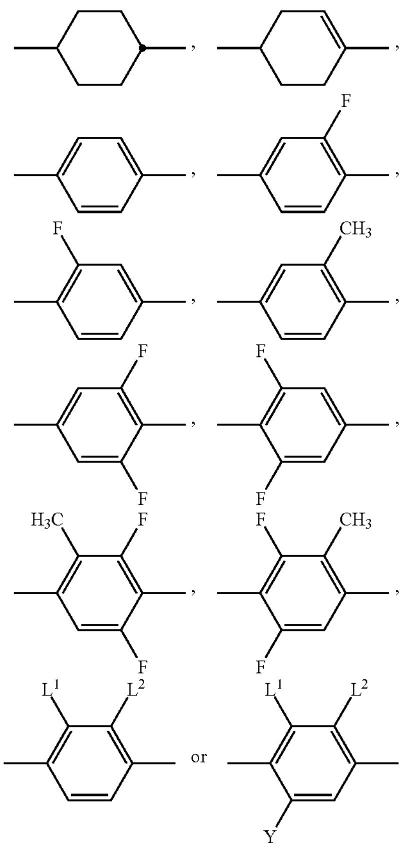

$L^1$, $L^2$ each, independently of one another, denote F, Cl, $CH_3$ or $OCH_3$, and

Y $CH_3$, $CH_2CH_3$.

3. The compound according to claim 1, wherein n is 1 or 2.

4. The compound according to claim 1, wherein $Z^0$ is a single bond.

5. The compound according to claim 1, wherein the compound of formula I is selected from the group consisting of the following formulae:

I-1

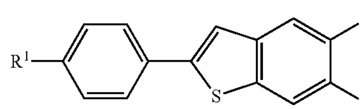

-continued
I-2
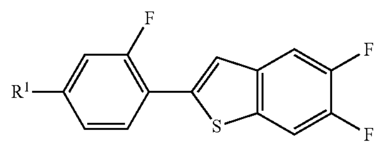
I-3
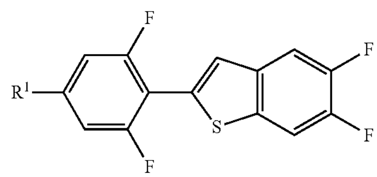
I-4
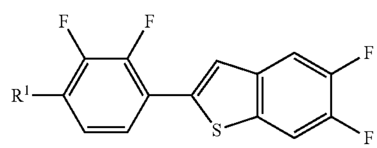
I-5
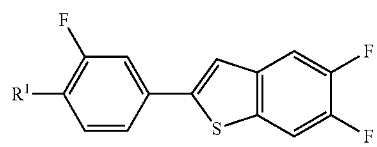
I-6
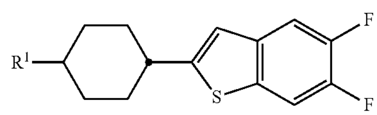
I-7
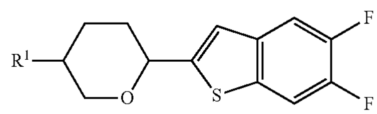
I-8
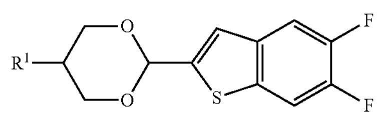
I-9
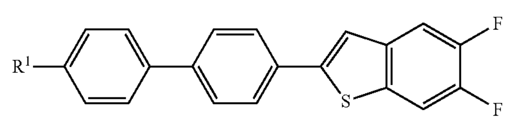
I-10
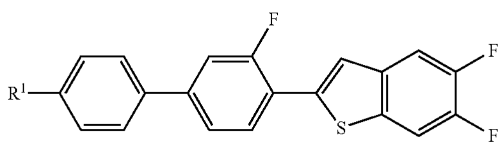
I-11
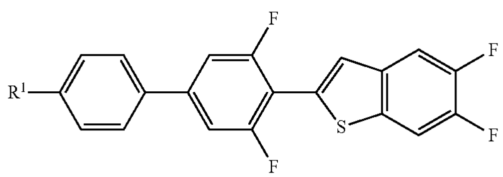

-continued
I-12
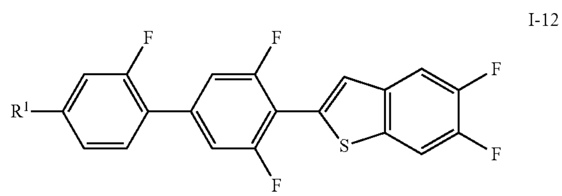
I-13
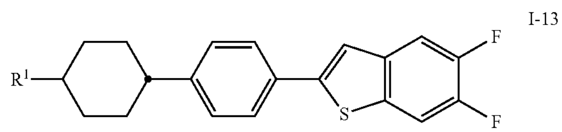
I-14
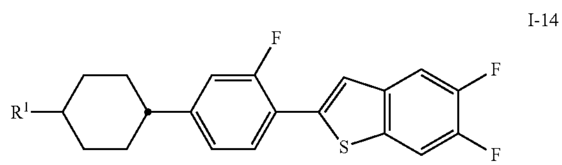
I-15
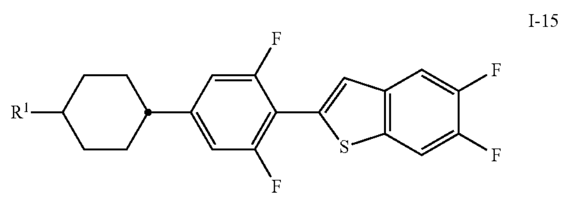
I-16
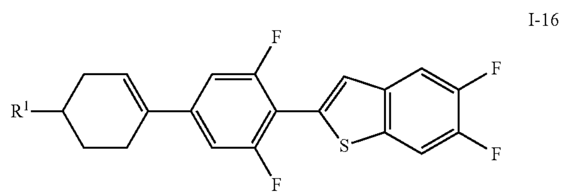
I-17
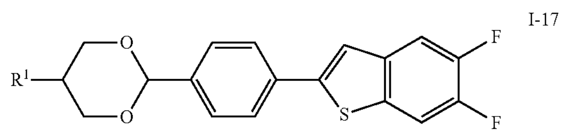
I-18
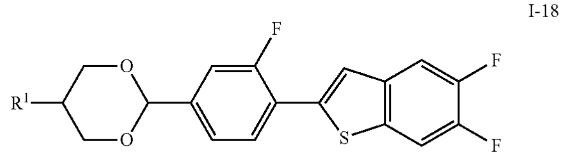
I-19
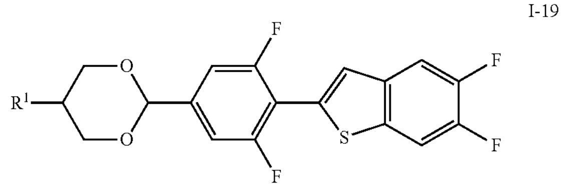
I-20
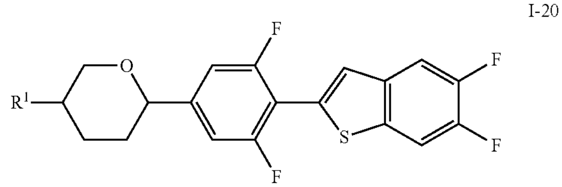

-continued

I-21

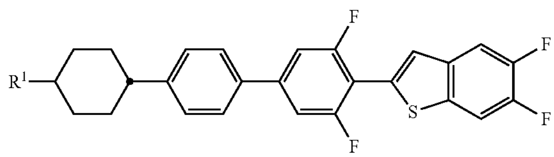

I-22

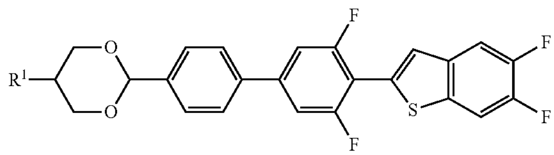

I-23

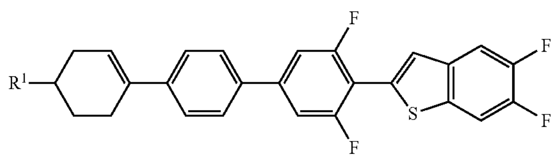

$R^1$ is an alkyl radical having 1 to 15 C atoms, wherein one or more $CH_2$ groups, including terminal C atoms, in this radical may each be replaced, independently of one another, by —C≡C—, —CH═CH—,

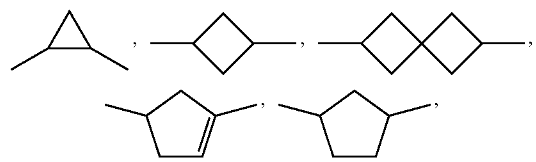

—O—, —S—, —(CO)—O—, —O—(CO)— in such a way that O or S atoms are not linked directly to one another, and in which, in addition, one or more H atoms may be replaced by F or Cl.

6. A liquid crystal mixture, comprising a compound of formula I according to claim 1.

7. A process for the production of a compound of formula I according to claim 1, comprising the steps of:

reacting a compound of formula I-S

I-S

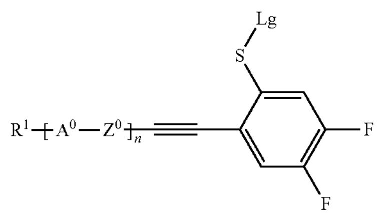

in which $R^1$ is an alkyl radical having 1 to 15 C atoms, wherein one or more $CH_2$ groups, including terminal C atoms, in this radical may each be replaced, independently of one another, by —C≡C—, —CH═CH—,

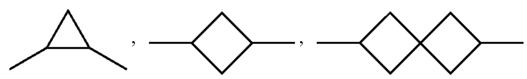

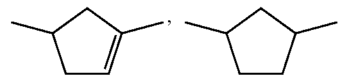

—O—, —S—, —(CO)—O—, —O—(CO)— in such a way that O or S atoms are not linked directly to one another, and in which, in addition, one or more H atoms may be replaced by F or Cl, $A^0$ independently of one another, on each appearance, denotes phenylene-1,4-diyl, in which, in addition, one or two CH groups may be replaced by N and one or more H atoms may be replaced by halogen, CN, $CH_3$, $CHF_2$, $CH_2F$, $OCH_3$, $OCHF_2$ or $OCF_3$, cyclohexane-1,4-diyl, in which, in addition, one or two non-adjacent $OH_2$ groups may be replaced, independently of one another, by O and/or S and one or more H atoms may be replaced by F, cyclohexene-1,4-diyl, bicyclo[1.1.1]pentane-1,3-diyl, bicyclo-[2.2.2]octane-1,4-diyl, spiro[3.3]heptane-2,6-diyl, tetrahydropyran-2,5-diyl or 1,3-dioxane-2,5-diyl, $Z^0$ independently denotes a single bond, $—CH_2O—$, —(CO)O—, $—CF_2O—$, $—CH_2CH_2CF_2O—$, $—CF_2CF_2—$, $—CH_2CF_2—$, $—CH_2CH_2—$, $—(CH_2)_4—$, —CH═CH—, —CH═CF—, —CF═CF— or —C≡C—, where asymmetrical bridges may be inserted in any orientation, n denotes 1, 2 or 3, and Lg is a leaving group, with a base to give a compound of the formula I.

8. A compound of formula I-S

I-S

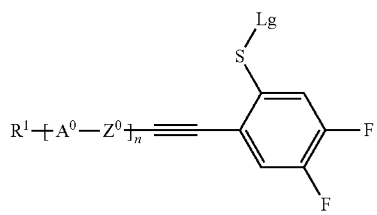

in which $R^1$ is an alkyl radical having 1 to 15 C atoms, wherein one or more $CH_2$ groups, including terminal C atoms, in this radical may each be replaced, independently of one another, by —C≡C—, —CH═CH—,

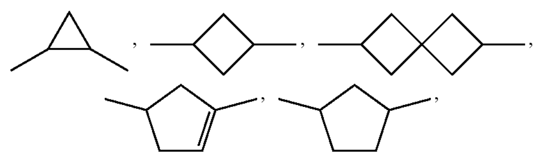

—O—, —S—, —(CO)—O—, —O—(CO)— in such a way that O or S atoms are not linked directly to one another, and in which, in addition, one or more H atoms may be replaced by F or Cl, $A^0$ independently of one another, on each appearance, denotes phenylene-1,4-diyl, in which, in addition, one or two CH groups may be replaced by N and one or more H atoms may be replaced by halogen, CN, $CH_3$, $CHF_2$, $CH_2F$, $OCH_3$, $OCHF_2$ or $OCF_3$, cyclohexane-1,4-diyl, in which, in addition, one or two non-adjacent $CH_2$ groups may be replaced, independently of one another, by O and/or S and one or more H atoms may be replaced by F, cyclohexene-1,4-diyl, bicyclo[1.1.1]pentane-1,3-diyl, bicyclo-[2.2.2]octane-1,4-diyl, spiro[3.3]heptane-2,6-diyl, tetrahydropyran-2,5-diyl or 1,3-dioxane-2,5-diyl, $Z^0$ independently denotes a single bond, $—CH_2O—$, —(CO)O—, $—CF_2O—$, $—CH_2CH_2CF_2O—$, $—CF_2CF_2—$, $—CH_2CF_2—$, $—CH_2CH_2—$, $—(CH_2)_4—$, —CH═CH—, —CH═CF—, —CF═CF— or —C≡C—, where asymmetrical bridges may be inserted in any orientation, n denotes 1, 2 or 3, and Lg is a leaving group.

9. A liquid-crystalline medium, comprising one or more compounds of formula I according to claim 1.

10. The liquid-crystalline medium according to claim 9, having a total concentration of the compounds of formula I in the medium as a whole of 1% by weight or more but less than 30% by weight.

11. An electro-optical display or electro-optical component, comprising a liquid-crystalline medium according to claim 9.

12. The liquid-crystalline medium of claim 9, further comprising one or more compounds of formula 1, 2, 3, 4, or 5:

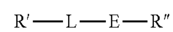 1

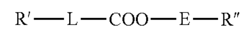 2

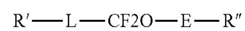 3

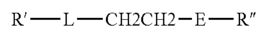 4

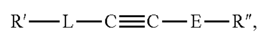 5 in which

L and E, which may be identical or different, each, independently of one another, denote a divalent radical from the group formed by the structural elements -Phe-, -Cyc-, -Phe-Phe-, -Phe-Cyc-, -Cyc-Cyc-, -Pyr-, -Dio-, -Py-, -G-Phe-, -G-Cyc- and their mirror images, where Phe denotes unsubstituted or fluorine-substituted 1,4-phenylene, Cyc denotes trans-1,4-cyclohexylene, Pyr denotes pyrimidine-2,5-diyl or pyridine-2,5-diyl, Dio denotes 1,3-dioxane-2,5-diyl, Py denotes tetrahydropyran-2,5-diyl and G denotes 2-(trans-1,4-cyclohexyl)ethyl, R' and/or R" each, independently of one another, denote alkyl, alkoxy, alkoxyalkyl, alkenyloxy or alkanoyloxy having 1 to 8 C atoms, alkenyl having 2 to 8 C atoms, —F, —Cl, —CN, —NCS or $—(O)iCH_3$-kFk, i is 0 or 1, and k is 1, 2 or 3.

* * * * *